Figure 1:
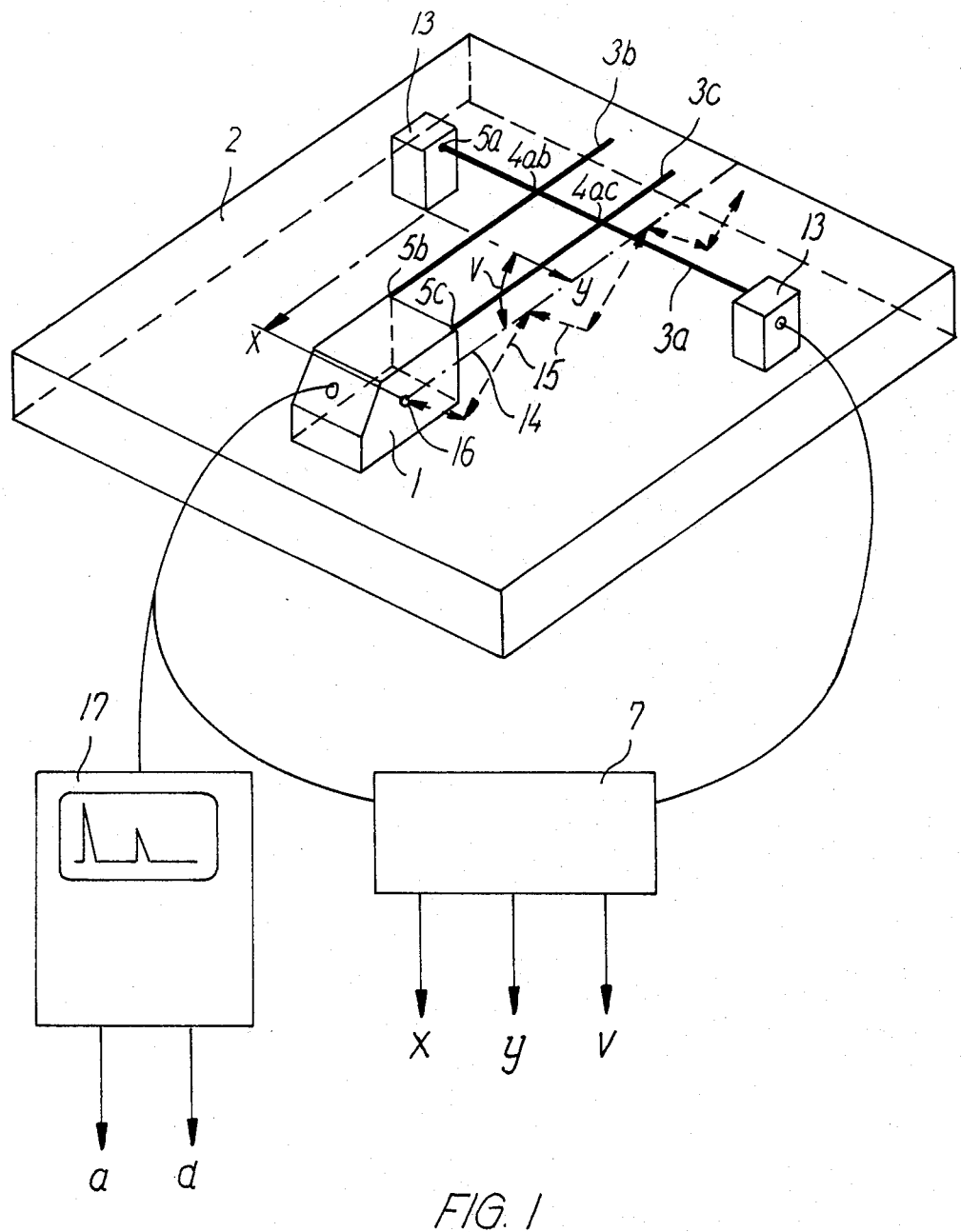

United States Patent [19]

Lund et al.

[11] Patent Number: 4,530,243

[45] Date of Patent: Jul. 23, 1985

[54] METHOD FOR DETERMINING THE POSITION OF A MEASURING SENSOR OR A PROBE

[75] Inventors: Svend A. Lund, Birkerod; Peter Krarup, Naerum; Thorkild Kristensen, Farum, all of Denmark

[73] Assignee: Akademiet for de Tekniske Videnskaber, Svejsecentralen, Glostrup, Denmark

[21] Appl. No.: 548,780

[22] Filed: Nov. 4, 1983

[30] Foreign Application Priority Data

Nov. 4, 1982 [DK] Denmark .............................. 4901/82

[51] Int. Cl.³ ...................... G01N 29/00; G05B 1/06
[52] U.S. Cl. ........................................ 73/633; 33/1 M; 318/666; 73/634
[58] Field of Search ................... 73/634, 633; 318/666; 33/1 M

[56] References Cited

U.S. PATENT DOCUMENTS

| 2,787,511 | 4/1957 | Ehret ...................................... 33/1 M |
| 3,585,851 | 6/1971 | Walther . |
| 3,663,881 | 5/1972 | Ehrenfried .......................... 318/666 |
| 3,898,838 | 8/1975 | Connelly .............................. 73/634 |
| 3,924,452 | 12/1975 | Meyer et al. . |
| 4,304,133 | 12/1981 | Feamster,III ......................... 73/633 |

Primary Examiner—Howard A. Birmiel
Attorney, Agent, or Firm—Banner, Birch, McKie & Beckett

[57] ABSTRACT

In an improved method for determining the position of a measuring sensor or probe (1), such as a probe for ultrasonic examination of an object (2), use is made of at least two mutually crossing bars (3a, 3b, 3c) of electrically conducting material in constant sliding, electrical contact with each other. At least one bar (3a) is kept fixed in relation to the object (2) to be examined, and at least one bar (3b, 3c) is kept fixed in relation to the probe (1). By measuring the electrical voltage drops in the bars, the positions of the crossing points (4ab, 4ac) between these bars and thereby the actual position of the probe in relation to a reference system (x, y) on the surface of the object are determined. By using at least three bars, it is possible to determine the position coordinates (x, y) as well as the angular direction (v) of a freely movable probe in relation to objects to be examined having plane, cylindrical or double-curved surfaces. Since the method can be carried out completely without use of movable and, thereby, vulnerable and complicated mechanical or electrical elements, scanning systems based on the method can be made considerably smaller, simpler, cheaper and more robust and reliable in operation than systems hitherto known.

7 Claims, 5 Drawing Figures

METHOD FOR DETERMINING THE POSITION OF A MEASURING SENSOR OR A PROBE

The invention relates to a method for determining the position of a measuring sensor or a probe, which is freely movable over and at a constant distance from the surface of an object to be examined, such as a sound probe for ultrasonic examination of the interior of the object.

In a number of methods for measuring and examining different materials and objects, use is made of measuring sensors or probes, which are freely movable in a two-dimensions movement over the surface of an object to be examined. Typical examples are the non-destructive testing by ultrasonic examination, in which an ultrasonic probe is moved over the surface of the object to be examined in constant contact with this surface, and by eddy current examination, by which an electric probe is moved over and at a constant distance from the surface of the object.

The objects to be examined will often have a plane surface, but they may also have a curved surface and may, for instance, be tubular objects or cylindrical vessels having dished ends of a double-curved configuration.

In manual examinations, an operator must for each single flaw indication measure and report the corresponding position and the angular direction of the probe in relation to the examined object. By mechanical-electrical scanning mechanisms a direct registration of the position and angular direction of the probe may be obtained at any time during the examination, but such automatic scanning mechanisms are often complicated and expensive to manufacture and maintain, and they have especially proved to be less useful in examinations, where the accessibility is very difficult and limited, as e.g. in examination of highly compact tube systems with many different tube dimensions.

It has, therefore, been tried to develop completely or partially contact-free methods for automatic acoustic and/or optical determination of the position of a freely movable and rotatable probe in relation to the surface of an object to be examined. Typical examples of such suggestions, i.e. with the use of optical-electrical methods with stationary, turnable or rotatable narrow parallelized light rays, are more closely described in DK patent specifications (applications Nos. 4953/81 and 548/82). However, it is a condition for most of these previously known systems that profiled guiding rails or guiding belts are clamped on the objects to be examined and that along these rails or belts selfmovable scanning carriages are moved. These systems may be difficult to manufacture sufficiently robust and reliable to be used under the coarse and dirty operational conditions, which are often present in examinations under industrial working and mounting conditions. Even in the most advanced methods, fast rotating mechanisms are still used, which may involve problems in use and maintenance under industrial condition.

It is an object of the present invention to indicate a method for determining the position of a measuring sensor or probe, which makes it possible to manufacture and use systems and devices which are completely without movable parts, and which may be made substantially more simple, cheaper and more robust and reliable than systems and devices hitherto known.

To obtain this, the method according to the invention is characterized in that use is made of at least two mutually crossing bars of an electrically conducting material, of which at least one is kept fixed in relation to the object to be examined and at least one is kept fixed in relation to the probe, at such distances from the surface of the object that the bars are constantly in sliding and electrical contact with each other at the crossing points, and that for each position of the probe an electrical current is made to flow successively through the bars and a measuring of the electrical voltage drop in the current-carrying bar from a predetermined reference point on the bar to the crossing point with the other bar or one of the other bars is at the same time carried out, this other bar being used as a measuring sensor for determining the voltage, after which the measured voltage drops are utilized in electronic calculating circuits to determine the actual position of the probe in relation to a predetermined reference system on the surface of the object to be examined.

Hereby is obtained that hitherto unknown and surprisingly simple scanning systems and devices can be manufactured, which are completely without movable vulnerable parts of any kind. The electric and electronic elements required for carrying out the method are all well known elements and integrated circuits which can be built together to completely encapsulated units with small dimensions and high reliability, even under the most coarse working conditions in practice. Furthermore, the units may be manufactured with such small dimensions that they can be used even under the most difficult accessibilities which can be met in practice.

An expedient embodiment of the method according to the invention is characterized in that use is made of one bar, which is kept fixed in relation to the object to be examined, and one bar, which is kept fixed in relation to the probe, the latter bar being maintained in a substantially constant angular direction in relation to the predetermined reference system on the surface of the object during the scanning of this surface.

In this way, the method is carried out as simple as can be imagined with the use of a minimum of units and electrical and electronic parts. In many cases in practice, such as routine examination of welding seams using ultrasound, it will be completely sufficient to use only a single constant scanning direction, substantially at right angles to the longitudinal direction of the weld. In other cases, the measuring sensor or probe will even not have an actual scanning direction, and the determination of a varying angular direction will then be completely superfluous.

Another embodiment of the method according to the invention is characterized in that use is made of one bar which is kept fixed in relation to the object to be examined, and at least two bars which are kept fixed in relation to the probe.

Hereby is obtained in the simplest conceivable manner and with a minimum of elements to be secured to the object to be examined, a determination of the position as well as the angular direction for a completely freely movable and turnable probe having one or more defined scanning directions.

A third expedient form of the method according to the invention is characterized in that use is made of at least two bars which are kept fixed in relation to the object to be examined, and one bar which is kept fixed in relation to the probe.

This is simply a symmetric version of what has just been described, and may be more expedient in some case in practice, e.g. in the ultrasonic examination of a welding seam having an irregular reinforcement in which case it may be most convenient to secure one bar on each side of the weld and parallel to the longitudinal direction thereof.

An expedient form of the method according to the invention to be used on an examined object having a cylindrical surface is characterized in that each bar which is kept fixed in relation to the object to be examined is arranged in a plane at right angles to the direction of generatrix of the object and is given such a curvature as to follow the surface of the object at a constant distance therefrom, and that each bar which is kept fixed in relation to the probe is made rectilinear and is preferably parallel to the scanning plane, if present, of the probe.

In this form, the method according to the invention can be carried out on tubular or solid cylindrical objects in exactly the same way as on objects having a plane surface, and it will, therefore, be especially suitable for ultrasonic examination of welding seams in complicated tube systems having a limited accessibility.

A suitable form of the method according to the invention to be used on an examined body having a substantially spherical surface is characterized in that each bar which is kept fixed in relation to the object to be examined is arranged in a plane parallel to a plane passing through the centre of the spherical surface and is given such a curvature that it follows the surface of the object at a constant distance therefrom, and that each bar which is kept fixed in relation to the probe is also given such a curvature that it follows the surface of the object at a constant distance therefrom and is arranged in a plane parallel to a plane passing at any time through the center of the spherical surface, the latter plane being preferably coincident with the scanning plane, if any, of the probe.

In this case, the method can be carried out on double-curved objects in exactly the same way as on objects having a plane surface, and it will, therefore, also be suitable for e.g. ultrasonic examination of dished ends of cylindrical containers.

A last expedient form of the method according to the invention is characterized in that in at least one of the points, in which two of the bars cross, an angle transducer is arranged being slidable in relation to both crossing bars and adapted to supply electrical signals representing at any time the actual angle between the two bars and thereby the actual angular direction of the probe in relation to the predetermined reference system on the surface of the object to be examined.

In some cases in practice, this form of the method may be expedient, partly because of a simplification of the required electrical and electronic circuit arrangement and/or, partly because it may permit a better and more secure electrical contact between the bars in the crossing point.

Figure 2:
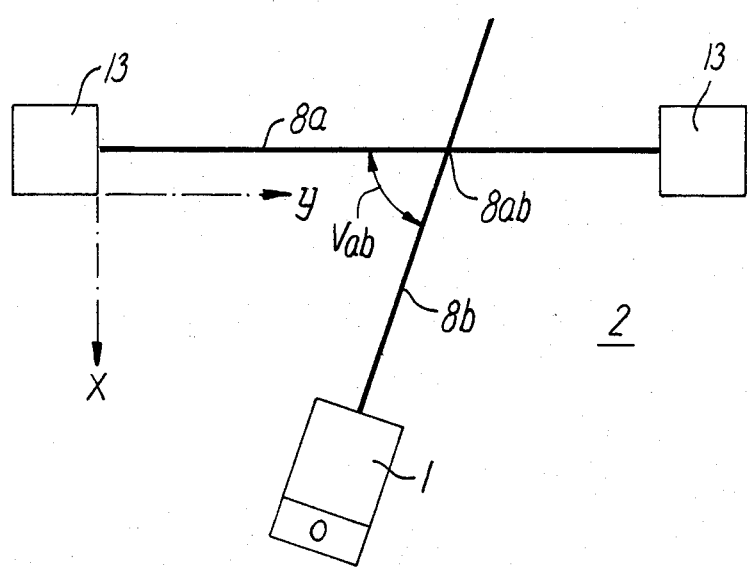
Figure 3:
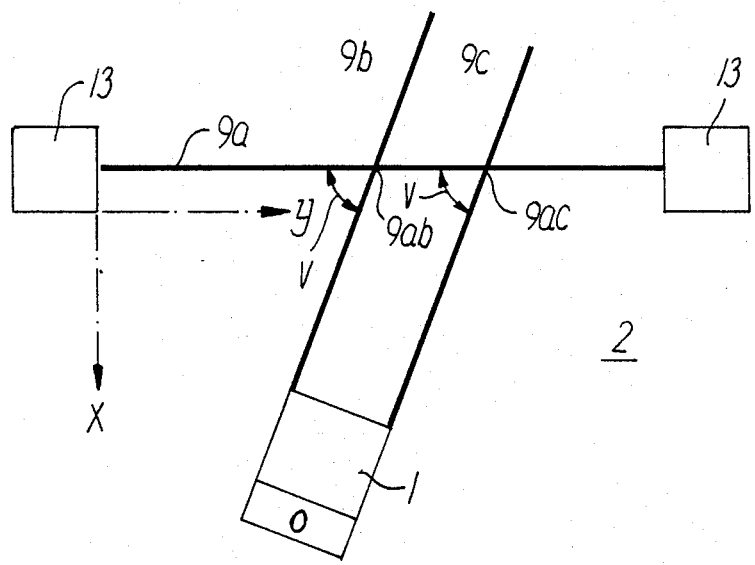
Figure 4:
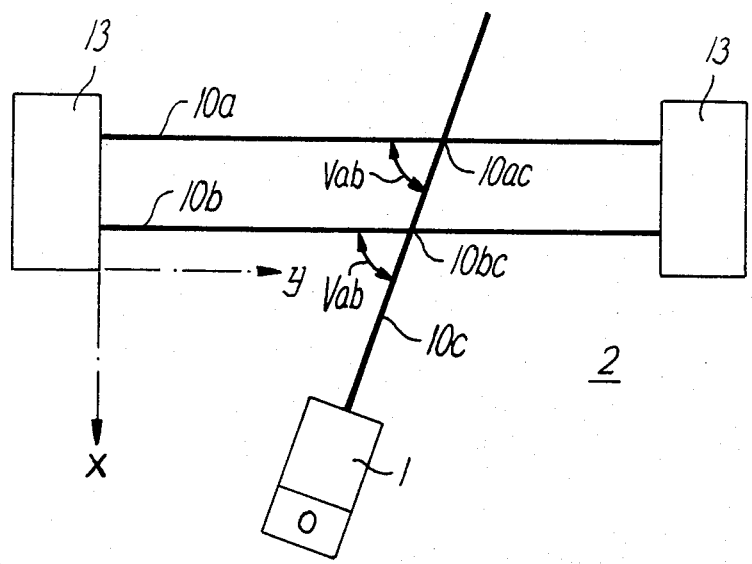
Figure 5:
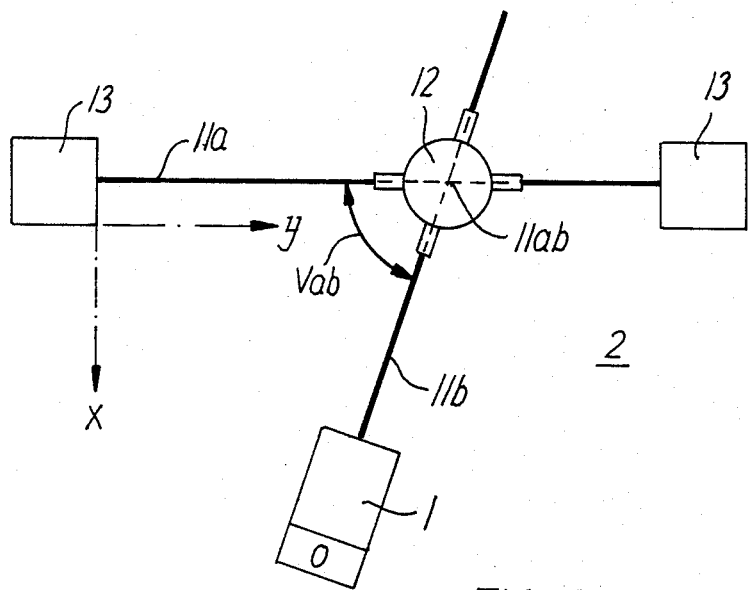

The invention will be explained more in detail in the following with reference to the schematic drawing, in which FIG. 1 shows the basic principle for carrying out the method according to the invention, FIG. 2 shows the principle of a form of the method according to the invention, FIG. 3 shows the principle of another form of the method according to the invention, FIG. 4 shows the principle of a third form of the method according to the invention, and FIG. 5 shows the principle of a last form of the method according to the invention.

FIG. 1 shows schematically a probe 1, which is freely movable and turnable over and in constant distance from the surface of an object 2 to be examined. In FIG. 1, the object is shown as having a plane surface, but it may, in principle, just as well have a cylindrical or double-curved surface. The probe may e.g. be an angle probe for the ultrasonic examination of the object by the pulse-echo method.

A narrow bar $3a$ of electrically conducting material is arranged at a constant distance from the surface of the object to be examined and is kept fixed in relation to the object 2 to be examined and thereby in relation to a predetermined reference system x, y on the surface of the object by means of movable holding devices 13. Two narrow bars $3b$ and $3c$ equally consisting of electrically conducting material are arranged at a constant distance from the surface of the object to be examined and are kept fixed in relation to the probe 1, in the case shown parallel to the scanning plane of the angle probe, i.e. parallel to the projection 14 of the sound path 15 on the surface of the object. The three bars are arranged at such distances from the surface of the object that the bar $3a$ is constantly in a sliding and electrical contact with the bars $3b$ and $3c$ in the crossing points $4ab$ and $4ac$.

The method according to the invention is then carried out in the following way.

For each single position of the probe, which it is desired to determine, an electrical current is successively made to flow through the bars, e.g. at first through the bar $3a$, then through the bar $3b$, and at last through the bar $3c$. While the bar $3a$ is carrying current, a measuring of the electrical voltage drop in this bar from a predetermined reference point $5a$ to the crossing point $4ab$ with the bar $3b$ is at first determined, the latter bar being used as a measuring sensor in the determination of the voltage. In connection with the known electrical resistance of the bar $3a$ and, thereby, the known voltage drop per longitudinal unit thereof, the measured voltage drop represents directly the actual distance along the bar $3a$ from the reference point $5a$ to the crossing point $4ab$.

Then a measuring is made of the voltage drop from the reference point $5a$ to the crossing point $4ac$ on the bar $3c$, which is now used as a measuring sensor in determining the voltage. The voltage drop thus measured represents directly the actual distance along the bar $3a$ from the reference point $5a$ to the crossing point $4ac$.

Then an electrical current is made to flow through the bar $3b$, and a measuring is made of the voltage drop from the reference point $5b$ on this bar to the crossing point $4ab$ with the bar $3a$, the latter bar being now used as a measuring sensor in determining the voltage. Finally, an electrical current is made to flow through the bar $3c$, and at the same time a determination is made of the voltage drop from the reference point $5c$ on this bar to the crossing point $4ac$ with the bar $3a$, the latter bar being once more used as a measuring sensor. The voltage drops thus measured directly represent the actual distances along the bars $3a$ and $3c$ from the point $5b$ to the point $4ab$ and from the point $5c$ to the point $4ac$, respectively.

Three of the four electrical voltage drops thus measured unambiguously determine the actual position coordinates x, y of the sound emission point 16 of the probe and the angular direction v of the projection 14 of the ultrasonic path in relation to the reference system on the surface of the object to be examined. The fourth measured voltage drop can, if desired, be used as a check or to improve the measuring accuracy of the determination of the position.

The measured voltage drops are used by means of electronic calculating circuits 7 to calculate and generate electrical coordinate signals x, y and v, which can be adapted to and transmitted to any known device for automatic registration and storing of the results of the examination carried out. In the embodiment shown, the ultrasonic probe is connected to a usual ultrasonic instrument 17, which by means of a measuring of the intensity and transit time of reflected ultrasonic pulses can generate and transmit electrical amplitude signals a and distance signals d, representing the length of the sound path 15 traversed by the ultrasonic pulses. The five output signals shown are e.g. just sufficient to produce and register in known manner the complete projection and section images showing the position and magnitude of the reflecting faults in the interior of the object being examined.

The measuring bars to be used may principally have any desired shape, when only the crossing points 4ab and 4ac are sufficiently well defined for the purpose in question, and they may be manufactured from any desired electrically conducting material, when only the electrical resistance of the material is so high that the measured voltage drop can be determined with the required accuracy for the present purpose.

An immediate possibility will be for the bars to use small thin-walled tubes, so-called cannula tubes, of stainless steel. Investigations in practice have shown that such tubes in lengths of abt. 200 mms are sufficiently robust for the purpose and give a sufficiently small contact resistance in the crossing points, and that with such tubes sufficiently high measuring speed and an accuracy in the determination of the position of a few tenths of a millimeter can be obtained without further measures, which will be more than sufficient for most practical measuring and examination purposes. Another obvious solution would be to shape the bars as stretched strings of electrical resistance wire, whereby very precisely defined crossing points having a very little contact resistance can be maintained and determined. In both said cases, it will be possible to increase and secure the measuring accuracy by holding the bars pressed against each other at any time by means of spring loading or another suitable preloading.

The electrical system for feeding the bars with current and for the voltage measuring can be designed in many different obvious ways using direct current as well as alternating current. An obvious possibility would be to use a low-ohmic system comprising a constant current source for supplying the current and a high-ohmic system for measuring the voltage drops in the bars. To increase the measuring accuracy, it is furthermore possible to use a running calibration by carrying out simultaneous reference measurements of the electrical voltages at both ends of the free lengths of the current conducting bars.

The electronic calculating circuit arrangements 7 for calculating and utilizing the measured voltage drops can also be designed in many different known and expedient ways for the present purpose and can by an expert within the field concerned be assembled from existing readymade integrated circuits, which are generally accessible in the trade.

FIG. 2 shows the principle of the most simple form imaginable of the method according to the invention in which use is made of one bar 8a, which is kept fixed in relation to the object to be examined, and one bar 8b, which is kept fixed in relation to the probe 1. In this case, the determination of the varying angular direction of the probe is renounced and the probe, therefore, has to be moved at a substantially constant angular direction in relation to the predetermined reference system x, y on the surface of the object.

From the known angle $v_{ab}$ and a running measurement of the voltage drops in the bars in exactly the same way as explained above, electrical measuring signals representing the actual position coordinates x, y of the probe can at any time be generated.

FIG. 3 shows the principle of the form of the method according to the invention described in detail above in connection with FIG. 1, shown here in projection on the surface of the object 2, use being made of one bar 9a which is kept fixed in relation to the object, and two bars 9b and 9c which are kept fixed in relation to the probe 1.

FIG. 4 shows a corresponding principle in the third form of the method according to the invention. In this form, which is symmetrical in relation to FIGS. 1 and 3, use is made of two bars 10a and 10b, which are kept fixed in relation to the object 2, and one bar 10c which is kept fixed in relation to the probe 1. From a running measurement of the voltage drops in the bars, principally in exactly the same way as described above in connection with FIG. 1, electrical measuring signals representing the actual position x, y and angular direction $v_{ab}$ of the probe in relation to the predetermined reference system on the surface of the object can at any time be generated.

FIG. 5 shows the principle of a last form of the method according to the invention corresponding to FIG. 2, in which use is made of one bar 11a which is kept fixed in relation to the object 2, and one bar 11b which is kept fixed in relation to the probe 1. In the crossing point 11ab between the two bars, an ordinary angle transducer 12 ia arranged so as to be slidable in relation to the two crossing bars, said transducer supplying electrical signals representing at any time the actual angle $v_{ab}$ between the two bars and, thereby, the actual angular direction of the probe in relation to the predetermined reference system on the surface of the object 2. By this addition, it is possible by means of only two bars to generate the required measuring signals for the running determination of the actual position x, y, and angular direction $v_{ab}$ of the probe in relation to the reference system on the surface of the object.

The method according to the invention has until now been described by its use in connection with objects having plane surfaces, but principally it can just as well be used in connection with tubular objects or cylindrical containers or vessels. In this case it is only required that the bar or bars 3a, 8a, 9a, 10a, 10b or 11a, shown in FIGS. 1 to 5, which are kept fixed in relation to the object to be examined, are arranged in planes in right angles to the direction of generatrix of the object and are given such curvatures that they follow the surface of the object at a constant distance therefrom and, furthermore, that the bar or bars 3a, 3c, 8b, 9b, 9c, 10c or 11b, which are kept fixed in relation to the probe 1, are made rectilinear and are preferably arranged parallel to a scanning plane, if present, thereof.

As long as the angle between the crossing bars varies only within a small area about 90°, the method can in most applications, especially in connection with objects having greater radii of curvature, be carried out directly with sufficient accuracy, exactly as described above in connection with FIGS. 1 to 5, the position coordinate y being simply determined along the curved surface of the cylindrical object. By required greater variations of the angular direction and by objects having smaller radii of curvature, it will, as a matter of course, be possible to arrange the electronic calculating circuit arrangement 7 in such known way as to carry out the required corrections in the calculation of the coordinate, taking into consideration the geometric shape of the object.

In a corresponding way, the method acording to the invention can principally just as well be used in examining objects having substantially spherical surfaces, such as spherical containers or dished ends of cylindrical containers. In this case, it is only required that the bar or bars 3a, 8a, 9a, 10a, 10b or 11a, shown in FIGS. 1 to 5, and being kept fixed in relation to the object 2, are each arranged in a plane parallel to a plane through the centre of the spherical surface and are given such a curvature that they follow the surface of the object at a constant distance therefrom and that, furthermore, the bar or bars 3b, 3c, 8b, 9b, 9c, 10c or 11b, which are kept fixed in relation to the probe 1, are also given such curvature as to follow the surface of the object at a constant distance therefrom, and are also each arranged in a plane parallel to a plane passing at any time through the center of the spheric surface, said latter plane being preferably coincident with the scanning plane, if present, of the probe.

As long as the angle between the crossing bars varies only within a small area about 90°, the method can in most applications, especially in connection with objects having greater radii of curvature, be carried out directly with sufficient accuracy, completely as described above in connection with FIGS. 1 to 5, the position coordinates x and y being simply determined along the curved surface of the object. With greater variations of the angular direction, and in connection with objects having smaller radii of curvature, it will be possible, as a matter of course, to arrange the electronic calculating circuit arrangements 7 in such a way as to carry out the calculation of the coordinates in a proper spheric coordinate system and with the required corrections with a view to the geometric shape of the object.

The method according to the invention has been described above mainly in connection with ultrasonic examination as an example of application. However, it is obvious to an expert that the general principles for carrying out the method can just as well be used in the determination of the position of measuring sensors or probes for numerous other purposes within the measuring and examination technique. As a simple typical and obvious purpose of application within the measuring technique, the automatic measuring by planimetering of irregularly shaped closed curves on plane, cylindrical or spherical surfaces. By means of a guiding equipment as described above and with the addition of known further electronic calculating circuit arrangements, it will thus be possible to guide a measuring sensor or measuring stylus along the circumference of a closed curve and thereby obtain a direct automatic reading or registration of the length of the circumference of the curve and of the encircled area and, if desired, the moments of resistance and inertia of this area above desired sectional axes.

On the basis of the principle directions according to the invention, an expert conversant with the known technique for automatic generating, measuring, transferring, registering and storing of electrical signals and with automatic electronic calculations on the basis of such signals can immediately carry out the method according to the invention in many different obvious ways and for many different obvious purposes of application. The different forms and purposes of application described in detail above must, therefore, only be regarded as illustrative, but absolutely not as exhaustive examples on the practicing of the method according to the invention. The elements and the automatic controlling, measuring, registering and calculating circuit arrangements etc., required for carrying out the method according to the invention belong all per se to the known technique and can, therefore, be shaped, arranged and connected together in many different suitable and obvious ways to the present purpose without the devices thus produced and the method for their practical use therefore coming without the area limited by the principal ideas of the invention.

We claim:

1. A method for determining the position of a measuring sensor or probe, which is freely movable over and at a constant distance from the surface of an object to be examined, such as a sound probe for ultrasonic examination of the interior of the object, comprising the steps of arranging at least one bar of an electrically conducting material in fixed relation to the object to be examined and at a certain distance from the surface thereof, arranging at least one other bar of electrically conducting material in fixed relation to the probe and in such position as to be constantly in sliding and electrical contact at a crossing point with the at least one bar when the probe is moved over the surface of the object, applying for each measuring position of the probe an electrical current to the bars, measuring the voltage drop in a current carrying bar from a reference point on that bar to the crossing point with another bar, said other bar serving as a measuring sensor for determining the voltage drop, and determining the actual position of the probe in relation to a reference system on the surface of the object to be examined by applying the measured voltage drops to an electronic calculating circuit.

2. A method according to claim 1 wherein a first bar is arranged in fixed relation to the object to be examined and a second bar is arranged in fixed relation to the probe, which further comprises maintaining said second bar at a substantially constant angle in relation to the reference system on the surface of the object during the examination of this surface.

3. A method according to claim 1 wherein one bar is arranged in fixed relation to the object to be examined and at least two other bars are arranged in fixed relation to the probe.

4. A method according to claim 1 wherein at least two bars are arranged in fixed relation to the object to be examined and one bar is arranged in fixed relation to the probe.

5. A method according to claim 1, 2, 3 or 4 wherein said object to be examined has a cylindrical surface which further comprises arranging each bar which is in fixed relation to the object to be examined in a plane at right angles to the direction of the axis of the object, said bar having a curvature which follows the surface of the object at a constant distance therefrom and arranging each bar which is fixed in relation to the probe to be rectilinear and parallel to a scanning plane of said probe.

6. A method according to claim 1, 2, 3 or 4 wherein the body to be examined has a substantially spherical surface which further comprises arranging each bar which is in fixed relation to the object to be examined in a plane parallel to a plane passing through the center of said spherical surface, said bar having a curvature which follows the surface of the object at a constant distance therefrom, and arranging each bar which is fixed in relation to the probe in a plane parallel to a plane passing through the center of the spherical surface, said latter bar having a curvature which follows the surface of the object at a constant distance therefrom.

7. A method according to claim 1, 2, 3 or 4 wherein an angle transducer, slideable in relation to bars which are in sliding and electrical contact is positioned at the crossing point of said bars and is adapted to supply electric signals representing at any time the actual angle between the bars and thereby the actual angular direction of the probe in relation to the reference system on the surface of the object to be examined.

* * * * *